US009833589B2

(12) United States Patent　(10) Patent No.: US 9,833,589 B2
Heinonen　(45) Date of Patent: Dec. 5, 2017

(54) APPARATUS AND METHOD FOR SUPPLYING ANESTHETIC AGENT AND ANESTHESIA SYSTEM FOR PROVIDING INSPIRATION GAS TO LUNGS OF A SUBJECT

(71) Applicant: GENERAL ELECTRIC COMPANY, Schenectady, NY (US)

(72) Inventor: Erkki Heinonen, Helsinki (FI)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 837 days.

(21) Appl. No.: 14/102,891

(22) Filed: Dec. 11, 2013

(65) Prior Publication Data

US 2014/0158122 A1　Jun. 12, 2014

(30) Foreign Application Priority Data

Dec. 11, 2012　(EP) .................................. 12196405

(51) Int. Cl.
*A61M 16/01*　(2006.01)
*A61M 16/10*　(2006.01)
(Continued)

(52) U.S. Cl.
CPC ........ *A61M 16/104* (2013.01); *A61M 16/186* (2013.01); *A61M 16/01* (2013.01);
(Continued)

(58) Field of Classification Search
CPC .... A61M 16/01; A61M 16/104; A61M 16/18; A61M 16/186; A61M 11/04–11/048
See application file for complete search history.

(56) References Cited

U.S. PATENT DOCUMENTS 3,831,599 A * 8/1974 Needham ............ A61M 16/186
128/203.12
4,058,120 A * 11/1977 Caparrelli ........... A61M 16/186
128/203.12
(Continued)

FOREIGN PATENT DOCUMENTS

CN　101472631 A　7/2009
CN　201692468 U　1/2011
(Continued)

OTHER PUBLICATIONS

European Search Report dated May 24, 2013 which was issued in connection with EP Patent Application No. 12196405.0 which was filed on Dec. 11, 2012.

(Continued)

*Primary Examiner* — Valerie L Woodward

(57) ABSTRACT

An apparatus and method for supplying anesthetic agent to an anesthesia system. The system is connecting detachably with at least two such apparatuses. The apparatus includes a storage volume for a liquid anesthetic agent and a space for evaporating the liquid agent. The apparatus also includes a gas inlet port for receiving a fresh gas for mixing with evaporated agent and a gas outlet port for conducting the gas mixture including evaporated agent to the system. The apparatus also includes a logic circuit for controlling anesthetic agent supply and an apparatus signal connector to exchange information. The apparatus signal connector includes at least one first apparatus contact for receiving from the system a signal indicating whether anesthetic agent supply is allowed or prevented, and a second apparatus contact to indicate that this apparatus is configured to supply anesthetic agent.

20 Claims, 2 Drawing Sheets

(51) Int. Cl.
*A61M 16/18* (2006.01)
*A61M 16/22* (2006.01)

(52) U.S. Cl.
CPC ............. *A61M 16/10* (2013.01); *A61M 16/22* (2013.01); *A61M 2205/6027* (2013.01)

(56) References Cited

U.S. PATENT DOCUMENTS

| | | | |
|---|---|---|---|
| 4,307,718 A | 12/1981 | Schreiber | |
| 4,346,701 A | 8/1982 | Richards | |
| 4,611,590 A | 9/1986 | Ryschka et al. | |
| 4,982,734 A * | 1/1991 | Green | A61M 16/186 128/200.14 |
| 5,293,865 A * | 3/1994 | Altner | A61M 16/186 128/202.27 |
| 5,537,992 A * | 7/1996 | Bjoernstijerna | A61M 16/1015 128/200.19 |
| 5,810,001 A | 9/1998 | Genga et al. | |
| 5,921,235 A * | 7/1999 | Kronekvist | A61M 16/186 128/203.12 |
| 6,216,690 B1 * | 4/2001 | Keitel | A61M 16/104 128/203.12 |
| 6,302,104 B1 | 10/2001 | Kronekvist | |
| 6,962,153 B2 | 11/2005 | Gershteyn | |
| 7,472,700 B2 | 1/2009 | Gershteyn | |
| 2002/0069876 A1 * | 6/2002 | Loser | A61M 16/18 128/203.19 |
| 2005/0072420 A1 | 4/2005 | Gershteyn | |
| 2006/0278220 A1 * | 12/2006 | Schermeier | A61M 16/186 128/203.12 |
| 2009/0194103 A1 * | 8/2009 | Thom | A61M 16/104 128/203.12 |
| 2009/0266358 A1 | 10/2009 | Sacristan Rock et al. | |
| 2011/0000488 A1 * | 1/2011 | Blomberg | A61M 16/104 128/203.14 |
| 2011/0056490 A1 * | 3/2011 | Kullik | A61M 16/01 128/203.12 |
| 2011/0297148 A1 * | 12/2011 | Faber | A61M 16/186 128/203.12 |

FOREIGN PATENT DOCUMENTS

| | | |
|---|---|---|
| CN | 102046234 A | 5/2011 |
| EP | 0680770 A1 | 11/1995 |
| GB | 2418366 A | 3/2006 |
| WO | 93/10392 A1 | 5/1993 |
| WO | 2007147505 A2 | 12/2007 |

OTHER PUBLICATIONS

Unofficial English Translation of Chinese Office Action issued in connection with corresponding CN Application No. 201310668728.7 dated Oct. 10, 2016.

* cited by examiner

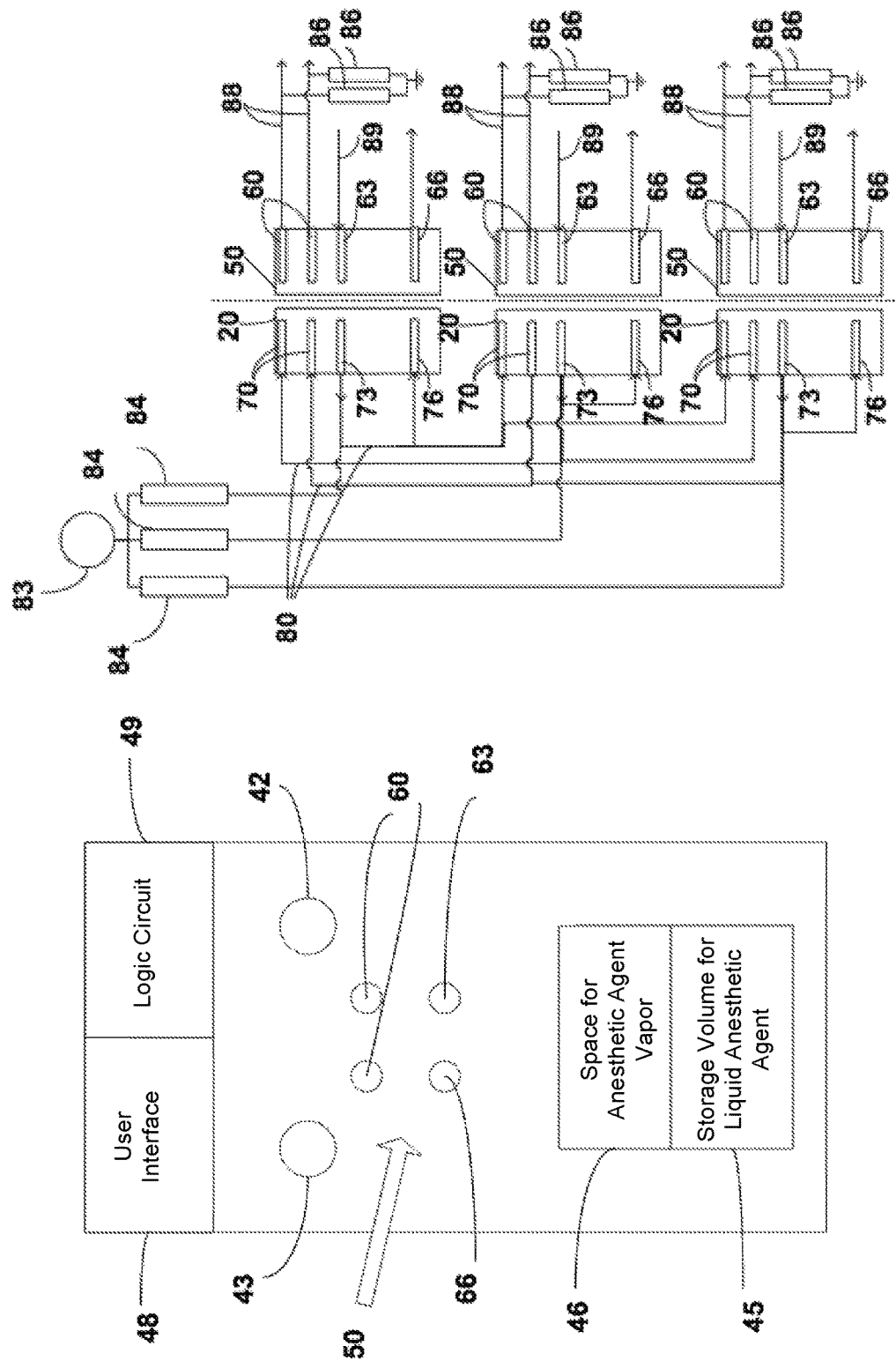

APPARATUS AND METHOD FOR SUPPLYING ANESTHETIC AGENT AND ANESTHESIA SYSTEM FOR PROVIDING INSPIRATION GAS TO LUNGS OF A SUBJECT

BACKGROUND OF THE INVENTION

This disclosure relates generally to an apparatus and a method for supplying anesthetic agent to an anesthesia system. The disclosure also relates to an anesthesia system for providing an inspiration gas to lungs of a subject.

On general anesthesia anesthetic drugs are used to induce and maintain patients experiencing surgical operation relaxed motionless, unconscious, and free from pain. The anesthetic drugs interfere on the central nervous system for these effects. On inhalation anesthesia anesthetic drugs are delivered through patient breathing to lungs where they get diffused to patient blood circulation. This circulation further carries the drug to the effect site in brains.

Inhalation anesthesia drugs are halogenated hydrocarbons that are delivered on administration site as liquids. These liquids are very volatile with vapor pressure at room temperature varying between 20-90 kPa. These liquids are vaporized for patient breathing in anesthesia vaporizer. The most common inhalation anesthesia drugs are isoflurane, sevoflurane and desflurane. These have replaced the use of their predecessors, halothane and enflurane.

For various reasons preference of the agent to be used may vary between patients and clinics. The vaporizers are heavy devices to enclose thermal energy for the cooling caused by liquid vaporization. The devices are positioned high over table top for convenient use of the output concentration dial. Therefore their installation on the anesthesia system may be laborious for clinical personnel. For this reason the anesthesia machines are equipped with functionality that enables easy selection of the agent to be used. Anesthesia system accommodates therefore often two or three sockets to connect the vaporizer. As separate, anesthesia system independent, module provides also advantage to have functional redundancy against vaporizer failure.

In operation, vaporizer receives fresh gas, which is a mixture of oxygen, nitrogen, and nitrous oxide, and completes that with required percentage of the anesthetic drug vapor. On state-of-the-art vaporizers the completion occurs with passive vaporization of the liquid agent respective to its vapor pressure. This prepared gas is then delivered from vaporizer outlet to anesthesia breathing system for further delivery to patient.

Arising from the principle of vaporization to the vapor pressure, if two vaporizers would be connected in series they both deliver the required concentration to the passing gas stream. Both of these drugs would then get delivered for patient breathing and circulation to effect-site both drug causing their effect resulting to doubled strength of the anesthesia effect. Clinically such situation is challenging to manage and therefore vaporizer constructional requirement standards require mechanisms that prevents simultaneous opening of the vaporizers.

State-of-the-art anesthesia systems include sockets to mount the vaporizers side-by side. The vaporizers designed for these sockets have mechanical pins protruding out from the vaporizer enclosure from its side adjacent to the other vaporizer when the vaporizer is activated from their concentration control dial. This protruding pin then prevents the other vaporizers connected to the system get activated when their pin have no more room for protrusion in colliding with the pin of the already activated vaporizer. These anesthesia systems are designed for mechanical vaporizers.

Modern anesthesia systems are electronic except the vaporizers where the traditional mechanical actuation including interlocking and passive vaporization still dominates. These devices lack in performance what electronics can bring along regarding e.g. therapy data recording to patient records, diagnostics, measuring drug usage, monitoring drug level and external control of the desired output from anesthesia system.

Electronics as part of anesthesia vaporizer would thus bring many benefits to the anesthesia system. Provision of the mechanical interlock with moving parts and arms is however impractical electronically in requiring mechanical movement. Such systems would require actuators generating this movement as well as sensors sensing whether the movement of adjacent vaporizer has occurred preventing the opening of another vaporizer.

External electronic control of the vaporizer from anesthesia system allows positioning of the vaporizers beyond the prime user interface area as well as anesthesia automation. Provision of electrical energy for vaporization miniaturizes size and weight. These enable anesthesia system miniaturization, and even positioning of the vaporizer to prime user interface for manually control of the vaporizer from the embedded controls.

BRIEF DESCRIPTION OF THE INVENTION

The above-mentioned shortcomings, disadvantages and problems are addressed herein which will be understood by reading and understanding the following specification.

In an embodiment, an apparatus for supplying anesthetic agent to an anesthesia system, the system being configured to connect detachably with at least two such apparatuses, the apparatus includes a storage volume for a liquid anesthetic agent, and a space for evaporating the liquid anesthetic agent. The apparatus also includes a gas inlet port for receiving from the anesthesia system a fresh gas for mixing with evaporated anesthetic agent, and a gas outlet port for conducting the gas mixture including evaporated anesthetic agent out from the space to the anesthesia system. The apparatus further includes a logic circuit for controlling anesthetic agent supply to the anesthesia system, and an apparatus signal connector for detachably connecting with the anesthesia system to exchange information. The apparatus signal connector includes at least one first apparatus contact for receiving from the anesthesia system a signal indicating whether anesthetic agent supply to the anesthesia system is allowed or prevented, and a second apparatus contact to indicate that this apparatus is configured to supply anesthetic agent to the anesthesia system.

In another embodiment a method for supplying anesthetic agent from an apparatus to an anesthesia system, the system being configured to connect detachably with at least two such apparatuses, the method includes providing a signal communication between the apparatus and the anesthesia system, and preparing to activate anesthetic agent supply from the apparatus connected to the anesthesia system. The method also includes receiving in the apparatus a signal from the anesthesia system, and indicating based on the signal whether anesthetic agent supply to the anesthesia system is allowed or prevented. The method further includes transmitting a signal from the apparatus activated to supply anesthetic agent to the anesthesia system to indicate that this apparatus is configured to supply anesthetic agent to the anesthesia system.

In yet another embodiment, an anesthesia system for providing an inspiration gas to lungs of a subject includes a fresh gas mixer for preparation of the fresh gas mixture, and an apparatus for supplying anesthetic agent. The anesthesia system also includes an interface device with at least two sockets, each socket being for detachably connecting one such apparatus for supplying anesthetic agent. The interface device provides for each socket a gas output opening for delivering the fresh gas from the fresh gas mixer to the apparatus, and an input opening for receiving from the apparatus the fresh gas mixed with anesthetic agent. The interface device also provides for each of the sockets an interface signal connector for signal communication between the interface signal connectors. The apparatus for supplying anesthetic agent includes a storage volume for a liquid anesthetic agent, and a space for evaporating the liquid anesthetic agent. The apparatus also includes a gas inlet port for receiving from the gas output opening of the interface device the fresh gas for mixing with evaporated anesthetic agent, and a gas outlet port for conducting the gas mixture including evaporated anesthetic agent out from the space to the gas input opening of the interface device. The apparatus further includes a logic circuit for controlling anesthetic agent supply to the interface device of the anesthesia system, and an apparatus signal connector for detachably connecting with the interface signal connector and for exchanging information with the interface signal connector. The interface signal connector includes at least one first interface contact for transmitting a signal indicating an operational state of other apparatus connected to other socket, and one second interface contact for receiving an INACTIVE signal to inactivate other apparatus connected to other socket. The apparatus signal connector includes at least one first apparatus contact for receiving from the first interface contact of the interface signal connector a signal indicating an operational state of other apparatus connected to other socket, and a second apparatus contact for transmitting the INACTIVE signal to the second interface contact to indicate that this apparatus is configured to supply anesthetic agent.

In yet another embodiment, an apparatus for supplying anesthetic agent to an anesthesia system, the anesthesia system having an interface device with at least two sockets, each socket being for detachably connecting one apparatus for supplying anesthetic agent to the anesthesia system, the interface device providing for each socket a gas output opening for delivering a fresh gas from the anesthesia system to the apparatus and an input opening for receiving from the apparatus the fresh gas mixed with anesthetic agent, and the interface device providing for each of the sockets an interface signal connector for signal communication between the interface signal connectors, the apparatus includes a storage volume for a liquid anesthetic agent, and a space for evaporating the liquid anesthetic agent. The apparatus also includes a gas inlet port for receiving from the gas output opening of the interface device the fresh gas for mixing with evaporated anesthetic agent, and a gas outlet port for conducting the gas mixture including evaporated anesthetic agent out from the space to the gas input opening of the interface device. The apparatus further includes a logic circuit for controlling anesthetic agent supply to the interface device, and an apparatus signal connector for detachably connecting with the interface signal connector and for exchanging information with the interface signal connector. The apparatus signal connector includes at least one first apparatus contact for receiving from the interface signal connector a signal indicating an operational state of other apparatus connected to other socket, and a second apparatus contact to indicate that this apparatus is configured to supply anesthetic agent to the anesthesia system.

Various other features, objects, and advantages of the invention will be made apparent to those skilled in the art from the accompanying drawings and detailed description thereof.

BRIEF DESCRIPTION OF THE DRAWINGS

FIG. 2 illustrates an apparatus for supplying anesthetic agent in accordance with an embodiment; and FIG. 3 illustrates an interlock communication in the anesthesia system interface for apparatuses for supplying anesthetic agents in FIG. 2 in accordance with an embodiment.

DETAILED DESCRIPTION OF THE INVENTION

Figure 1:
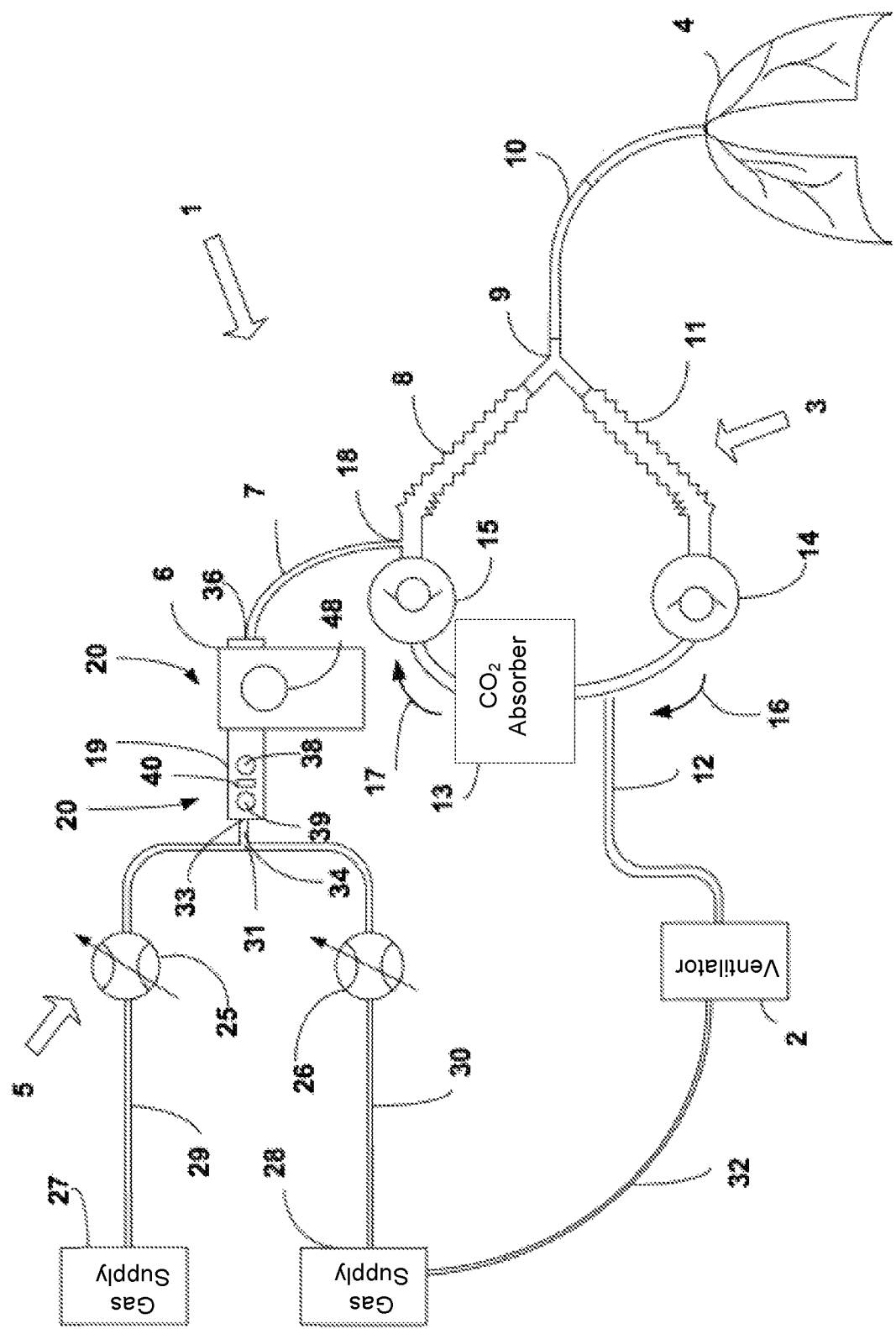
FIG. 1 illustrates an operational diagram of an anesthesia system comprising an apparatus for supplying anesthetic agent in accordance with an embodiment.

Specific embodiments are explained in the following detailed description making a reference to accompanying drawings. These detailed embodiments can naturally be modified and should not limit the scope of the invention as set forth in the claims.

An anesthesia system 1 for providing an inspiration gas to lungs of a subject shown in FIG. 1 may comprise a ventilator 2 for assisting breathing function of the subject, a breathing circuit 3 for connecting lungs 4 of the subject and the ventilator 2, a fresh gas mixer 5 for preparation of the appropriate breathing gas mixture of oxygen and nitrogen or nitrous oxide and to control its flow rate, and the apparatus 6 such as a vaporizer for supplying anesthetic agent to the fresh gas mixture received from the fresh gas mixer and which anesthetic agent mixed with the fresh gas mixture is supplied to the breathing circuit. The apparatus 6 is able to add anesthetic agent in user dialed concentration to the fresh gas flow. The apparatus comprises a user interface 48, such as a dial for providing a signal indicative of a concentration setting. The anesthesia system 1 can accommodate one or more apparatus. However, according to regulations, only one of the apparatus may be selected active at a time. The complete fresh gas mixture is conducted from the fresh gas mixer 5 and the apparatus 6 to the breathing circuit 3 through the fresh gas line 7.

In the breathing circuit 3 the fresh gas coming from the fresh gas mixer 5 and the apparatus 6 through a fresh gas outlet 18 is mixed with the re-circulated breathing gas at the circuit. During inspiration this mixture is guided through an inspiration line 8 to a branching unit 9 and further through a connection line 10 to subject lungs 4 expanding those. Expiration follows inspiration when the drive of the breathing gases into the lung is ceased. At this moment the compliant forces of the lungs pressurize the gas in the lungs. Expiration flow begins when the ventilator 2 opens an expiration control valve within the ventilator (not shown). Pressurized gas from the lungs 4 flows out through the connection line 10 to the branching unit and further through an expiration line 11 to a ventilator limb 12 and to the ventilator 2. Within the ventilator the exhalation gas is at least partially preserved for the next inspiration. At the time of the next inspiration, the expiration control valve of the ventilator 2 is closed, the inspiration control valve of the ventilator (not shown) is opened to drive at least partly the previously exhaled breathing gas from the ventilator 2 back to the breathing circuit 4. Now the inspiration gas flows through a CO2 absorber 13 to remove the patient exhaled carbon dioxide before getting inhaled again and through the inspiration line 8 where the fresh gas is added along a fresh gas line 7. An expiration valve 14 and inspiration valve 15 guide the direction of rotation of the ventilation within the breathing circuit as indicated by arrows 16 and 17. The fresh gas outlet 18 may be upstream to the inspiration line, but the fresh gas outlet can be also downstream the inspiration valve 15 as presented.

The anesthesia system also includes an interface device 19 to connect the apparatus 6 for supplying anesthetic agent to this interface device. The interface device 19 receiving fresh gas from the gas mixer 5 may comprise at least two sockets 20, each socket being for separate apparatus 6. In an embodiment, there is one socket for each apparatus for supplying anesthetic agent. The number of sockets is two in FIG. 1 accommodating maximum two apparatus the other socket being empty when only one apparatus module is connected, but naturally there can be more than that depending on the number of sockets in the interface device 19.

FIG. 1 shows the gas mixer for two gas channels both having control valve and measurement unit 25 and 26. The fresh gas is a mixture of oxygen, nitrogen and nitrous oxide. The gases are coming from pressurized gas supply 27 and 28 through lines 29 and 30. In FIG. 1 the pressure gas supply 27 is source for oxygen and the pressure gas supply 28 is for air. Metered gas flows are mixed together at connection point 31 and directed to an interface inlet 33 through gas line 34. From the interface device 19 the gas completed with requested concentration of anesthesia drug is guided from interface outlet 36 through the fresh gas line 7 to breathing circuit 3.

The ventilator 2 may be of any type common for anesthesia ventilation. These include pressure driven ventilators where the ventilator is powered using the supply pressure guided from pressurized gas supply 28 through a line 32 as presented on FIG. 1. The ventilator may be also electrically powered when the breathing circuit gas flow is induced using some electrically driven actuator.

Each socket of the interface device 19 may comprise a gas input opening 38 to receive the gas flow from the apparatus 6 for supplying anesthetic agent to the interface device and further to a fresh gas line 7. That may also have a gas output opening 39 to connect the gas flow from the gas line 34 to the apparatus 6. The interface device 19 provides for each socket 20 an interface signal connector 40, such as electrical connector, to connect to the apparatus 6 for transmitting signals to this apparatus and from this apparatus. This connection form may also be any applicable known signal transform means like optical or magnetic.

A schematic view of the apparatus 6 for supplying anesthetic agent vapor to breathing gas for subject breathing is shown in FIG. 2. The apparatus 6 may be a module detachable from the anesthesia system 1 and again remountable. Accordingly it can be said that the anesthesia system may connect detachably with at least two such apparatuses. The apparatus 6 may comprise an inlet port 42 for the fresh gas received from the gas output opening 39 of the interface device and an outlet port 43 for delivering vaporized anesthetic agent, which in an embodiment is mixed with the fresh gas, to the gas input opening 38 of the interface device 19 and which outlet port 43 is in flow communication with the fresh gas line 7 shown in FIG. 1. The apparatus 6 may also comprise a storage volume 45 for a liquid anesthetic agent. The liquid anesthetic agent originated in the storage volume 45 can be vaporized to a space 46 for anesthetic agent vapor, which space is also part of the apparatus 6. The gas coming from the gas inlet port 42 is guided through the space 46 to mix it with the anesthetic agent vaporized. The mixture is guided to the gas outlet port 43 for further delivering along the fresh gas line 7 to the breathing circuit 3 as shown in FIG. 1 for the subject breathing.

The apparatus 6 may also comprise as explained hereinbefore a user interface 48, such as a dial, for entering desired targeted amount of anesthetic agent on the apparatus 6 outlet flow for controlling the operation. The user interface may also be common with other parts of the anesthesia system 1 and does not necessarily be in the same apparatus module. Further the apparatus 6 may comprise a logic circuit 49, such as a processing unit, receiving a signal from the user interface 48 informing for instance a desired targeted amount of anesthetic agent at the apparatus output. This amount can be e.g. volumetric or mass concentration of the agent or partial pressure. The apparatus in FIG. 2 also comprises an apparatus signal connector 50, such as apparatus electrical connector, connecting with the interface signal connector 40 of the anesthesia system when mated.

A detailed signal communication between the apparatus 6 and the interface device 19 is shown in FIG. 3. The interface device as explained hereinbefore comprises at least two sockets 20 with interface signal connectors 40, gas input openings 38 and gas output openings 39 meaning that one apparatus 6 at a time can be connected to each socket. This means that if the number of socket is two, only two apparatus can be connected, but in the embodiment of FIG. 3 the number of sockets is three meaning that three apparatus can be connected to the interface device 19 at a time. When the apparatus is connected to the interface device besides both the gas inlet port 42 of the apparatus 6 is mating with the gas output opening 39 of the interface device and the gas outlet port 43 of the apparatus is mating with the gas input opening 38 of the interface device, but correspondingly the apparatus signal connector 50 is mating with the interface signal connector 40.

Each apparatus 6 or actually the apparatus signal connector 50 comprises at least one first apparatus contact 60 for an ENABLE input signal from other socket(s) or apparatuses, the number of these contacts being dependent on the number of sockets 20 or the number of apparatuses connectable to the anesthesia system simultaneously, which in an embodiment is equal to the number of other sockets in which case the number of first apparatus contacts is one less than the number of the sockets, and at least one second apparatus contact 63 for INACTIVE output signal. Further the apparatus 6 or actually the apparatus signal connector 50 may also comprise a third apparatus contact 66 for a status signal. Correspondingly each socket of the interface device comprises corresponding components, which are at least one first interface contact 70 for an ENABLE signal, the number of these contacts being dependent on the number of the sockets, which in an embodiment is equal to the number of other sockets, in which case the number of first interface contacts is one less than the number of the sockets (=number of sockets−1), and at least one second interface contact 73 for an INACTIVE signal. Further the interface socket may also comprise a third interface contact 76 for a status signal. When mating the apparatus and interface signal connectors also corresponding contacts on both sides are mated. All these apparatus contacts are communicating with the logic circuit 49 for processing the data. This processing includes control of whether anesthetic agent supply to the anesthesia system is allowed or prevented which information is based on the operational state of another apparatus connected to the anesthesia system. Activation of the apparatus is associated inspection of the system status signals to activate only when the activation is allowed. Furthermore, the logic circuit transmits the activation status to the interface device for the other apparatus connected to the interface device. Furthermore, the logic circuit may also cancel the apparatus activation in case apparatus cannot confirm communication of the activation status to the interface.

First interface contact(s) 70 for the ENABLE signal are connected to corresponding second interface contacts 73 for the INACTIVE signal of other socket(s) along signal lines 80 for creating a signal connection. In an embodiment the number of signal lines 80 connected to the interface signal connector 40 is the same as the number of first interface contacts 70 for the ENABLE signal of the socket 20. When the apparatus 6 is connected to the socket 20 and thus to the interface signal connector 40, the first apparatus contact(s) 60 for the ENABLE signal are in the signal connection with the second interface contact(s) 73 for the INACTIVE signal with other socket(s) and through the second interface contact(s) with the second apparatus contact(s) 63 of other apparatus(es) in case the other apparatus(es) is connected to the corresponding other socket(s). The first apparatus contact 60 for the ENABLE signal receives from the interface signal connector 40 a signal indicating an operational state of any other apparatus, which may be one of two options, the first option being whether any other apparatus is connected to any other socket is activated to supply anesthetic agent to the anesthesia system and the second option being whether all other apparatuses are inactivated from anesthetic agent supply to the anesthesia system.

For empty socket(s) this ENABLE signal defaults enabled allowing use of the anesthesia system 1 even not fully loaded. When apparatus 6 is connected that will control the ENABLE state of other apparatus(es) in the anesthesia system through the INACTIVE output. At the time of apparatus activation, the apparatus 6 or its logic circuit 49 first examines the state of its ENABLE input(s) in the first apparatus contact(s) 60. If they are on enable state then activation of the apparatus is allowed. In case any of the ENABLE input(s) received by the first apparatus contact(s) 60 would indicate another apparatus is already active on the anesthesia system the activation of the first apparatus is cancelled. If the signals indicate other apparatus(es) is/are inactive, activation of the apparatus will be allowed. Following activation the INACTIVE output of the first apparatus contact 63 state is changed to indicate the apparatus is active. This changes the ENABLE state of the other apparatus(es) to disable as well. This disables the other apparatus(es) from activation as explained above.

The INACTIVE signal is also signaled back or mirrored from the anesthesia system through the third interface 76 of the interface signal connector 40 to the third apparatus contact 66 for the STATUS signal and to the logic circuit 49 in order to confirm the INACTIVE signal is properly transmitted to the interface signal connector 40 or the anesthesia system, which acting may start for instance when using the user interface 48. This activation may occur also externally through communication line to apparatus 6 (not shown) from the anesthesia system 1. In an embodiment, all active components are positioned to the apparatus 6, while the interface device 19 is carrying only electrical lead wire with contacts. Mismatch between the mirrored STATUS signal and the original INACTIVE signal indicates connection problem between the apparatus 6 and the interface device 19. In this case the activation will be cancelled to stop agent delivery from the affected apparatus 6 to ensure only one apparatus connected to the anesthesia system 1 can be active and thus deliver anesthetic agent. Comparison of the signals is continuous to identify possible contact problems in the middle of vapor delivery as well. The STATUS defaults to inactive state to ensure active apparatus 6 is properly identified.

Default signal state at the apparatus signal connector 50 for the apparatus ENABLE is enabled. On the FIG. 3 logic this is logical high. This is done by connecting the apparatus enable contact 60 in the apparatus signal connector 50 to high voltage supply 83 using a resistor 84. Respective apparatus line defaults logical low. This is achieved by connecting the first apparatus contact 60 for the ENABLE signal to ground with resistor 86. With this arrangement, the signal for empty socket 20 is ENABLE allowing the apparatus 6 connected to the interface signal connector 40 stay enabled.

Default state of the apparatus 6 ENABLE lines 88, 89 being disabled prevents apparatus activation with broken connection to the apparatus signal connector 50. Obvious for the arrangement to function is that the ground and supply connection between the anesthesia system and the apparatus must be established (not shown).

For operation the resistance of the resistor 86 is large compared to the resistor 84. When connection fails, high resistance of resistor 86 is sufficient to pull down the ENABLE line, and when solid connection is established, low resistance 84 pulls up the line voltage.

Logical levels may as well be inverted to the presented one, i.e. logical low representing enabled and logical high representing disabled.

Hereinafter the operation of embodiments providing an interlock of electronic apparatus 6 for supplying anesthetic agent connected to the anesthesia system 1 are further explained. This interlock ensures at the time of activation other apparatus connected to the anesthesia system are inactivated thus preventing anesthetic agent supply. Furthermore, when the apparatus in the anesthesia system is activated any other apparatus(es) connected to the anesthesia system become disabled from activation as long as one of the apparatus in the anesthesia system is active and thus supplying anesthetic agent the anesthesia system. These interlock functions are operationally included in the apparatus module to maintain the advantage of modular approach to be able to remove and replace the apparatus to provide functional redundancy in case of module failure.

This interlock comprises electrical signal communication between the different apparatuses for supplying anesthetic agent where all active components are positioned to the apparatus module and the anesthesia system interface carrying only electrical signal lines 80 with interface contacts. This provides redundancy against device failures in a way that no single failure can interrupt inhalation anesthesia delivery and can be corrected by replacing the failed apparatus.

The apparatus 6 may communicate with the interface signal connector 40 through multi-pin electrical apparatus signal connector 50 engaging when the apparatus 6 is connected to the anesthesia system 1. This communication is using simple binary logic. Each apparatus 6 has an ENABLE input from all other apparatus sockets of the anesthesia system and INACTIVE output. Each ENABLE input is connected to INACTIVE output of another apparatus on the anesthesia system. For empty sockets this ENABLE defaults enabled allowing use of anesthesia system even not fully loaded.

Particular requirement for this interlocking system is safe operation in device- or communication failures. These failures include contact failure in ENABLE input and INACTIVE output of the apparatus 6 as well as device failure to turn the INACTIVE to disable state at time of activation.

In case of ENABLE input contact failure, the apparatus 6 connected to the socket 20 does not receive the enable state from the line. The apparatus receptacle for this enable pin defaults to disable, thus ENABLE pin contact failure prevents activation of the apparatus.

These described safety systems ensure the apparatus connected to anesthesia system can be activated only if the interlock communication to other apparatus connected is solid.

In this arrangement would two apparatus for supplying anesthetic agent be activated precisely at the same time, those both would set their INACTIVE lines to active. This will set the other apparatus ENABLE status to disable state and both of the apparatuses get disabled and inactivated.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for supplying anesthetic agent to an anesthesia system, the system being configured to connect detachably with at least two apparatuses, the system comprising:
    an interface device comprising a number of sockets, wherein the number of sockets is at least two, wherein at least one socket of the at least two sockets comprises an interface signal connector;
    a storage volume for a liquid anesthetic agent;
    a space for evaporating the liquid anesthetic agent;
    a gas inlet port for receiving a fresh gas for mixing with evaporated anesthetic agent;
    a gas outlet port for conducting the gas mixture including evaporated anesthetic agent out to the interface device;
    a logic circuit for controlling anesthetic agent supply to the anesthesia system; and
    an apparatus signal connector configured to detachably connect with the anesthesia system to exchange information and configured to mate with the interface device,
    wherein the apparatus signal connector comprises a number of first apparatus contacts configured to receive from the interface device a signal indicating whether anesthetic agent supply to the anesthesia system is allowed or prevented, and a second apparatus contact configured to indicate that this apparatus is configured to supply anesthetic agent to the anesthesia system, and
    wherein the interface signal connector is configured to mate with the apparatus signal connector.

2. The system of claim 1, wherein the second apparatus contact is configured to transmit an INACTIVE signal to inactivate any other apparatus connected to the anesthesia system.

3. The system of claim 2, wherein the apparatus signal connector also comprises a third apparatus contact to confirm that the INACTIVE signal was properly transmitted to the anesthesia system.

4. The system of claim 1, wherein each socket is configured to detachably connect one of the at least two apparatuses to the anesthesia system.

5. The system of claim 1, wherein the signal indicating whether anesthetic agent supply to the anesthesia system is allowed or prevented is based on an operational state of at least one of the at least two apparatuses connected to the anesthesia system.

6. The system of claim 5, wherein an operational state of at least one of the at least two apparatuses, is one of two options, the first option being whether the at least one of the at least two apparatuses is activated to supply anesthetic agent to the anesthesia system, and the second option being whether the at least one of the at least two apparatus is inactivated from anesthetic agent supply to the anesthesia system.

7. The system of claim 5, further comprising a user interface configured to change the operational state of the at least one of the at least two apparatuses to allow or to prevent mixing the evaporated anesthetic agent to the fresh gas received through the gas inlet port.

8. The system of claim 1, further comprising a user interface configured to provide a signal indicative of a concentration setting for the logic circuit.

9. The system of claim 8, wherein the user interface is configured to adjust anesthetic agent concentration.

10. The system of claim 1, wherein the number of first apparatus contacts is one less than the number of sockets.

11. The system of claim 1, wherein:
    each socket of the at least two sockets comprises a gas output opening and a gas input opening,
    wherein the gas output opening is configured to mate with the gas inlet port, and
    wherein the gas input opening is configured to mate with the gas outlet port.

12. A method for supplying anesthetic agent from at least two apparatuses to an anesthesia system using the system of claim 1, the method comprising:
    providing a signal communication between a vaporizer, the interface device, and the anesthesia system;
    activating the vaporizer to supply anesthetic agent to the anesthesia system;
    receiving in the vaporizer a first signal from the interface device;
    indicating based on the first signal whether the anesthetic agent supplied to the anesthesia system is allowed or prevented; and
    transmitting a second signal from the vaporizer activated to supply the anesthetic agent to the anesthesia system to indicate that the apparatus is configured to supply the anesthetic agent to the anesthesia system.

13. The method of claim 12, further comprising inactivating, based on the second signal, an other apparatus of the at least two apparatuses connected to the anesthesia system to prevent the supply of the anesthetic agent to the anesthesia system.

14. The method of claim 12, wherein whether anesthetic agent supply to the anesthesia system is allowed or prevented is based on an operational state of at least one apparatus of the at least two apparatuses connected to the anesthesia system, when the operational state of the at least one apparatus of the at least two apparatuses is one of two options, the first option being whether the at least one of the at least two apparatuses is activated to supply anesthetic agent to the anesthesia system, and the second option being whether the at least one of the at least two apparatuses is inactivated to prevent anesthetic agent be supplied to the anesthesia system.

15. The method of claim 14, further comprising transmitting a status signal from the interface device to the vaporizer to confirm that the second signal was properly transmitted from the apparatus to the anesthesia system.

16. The system of claim 1, wherein:
at least one apparatus of the least two apparatuses is configured to supply the anesthetic agent to the interface device and a vaporizer, the system further comprising:
a fresh gas mixer configured to prepare a breathing gas mixture.

17. The system of claim 16, wherein the fresh gas mixer is located upstream of the interface device and the vaporizer.

18. The system of claim 1, wherein the interface signal connector comprises an interface contact configured to transmit a status signal to confirm that an inactive signal to inactivate one of the at least two apparatuses was properly transmitted to the interface signal connector, and wherein the apparatus signal connector further comprises a third apparatus contact configured to receive the status signal to confirm that the interface signal connector received the inactive signal, indicating that the other apparatuses are inactivated to prevent anesthetic agent supply.

19. The system of claim 1, wherein a vaporizer is detachable and remountable to the sockets.

20. The system of claim 1, further comprising:
a ventilator configured to assist in the breathing function of a subject;
a breathing circuit configured to connect lungs of the subject and the ventilator, the breathing circuit comprising:
an inspiration line configured to provide an inspiration gas for the subject breathing;
an expiration line to discharge an expiration gas; and
a carbon dioxide absorber configured to remove carbon dioxide of the expiration gas.

* * * * *